United States Patent
Chin et al.

(10) Patent No.: US 7,248,348 B2
(45) Date of Patent: Jul. 24, 2007

(54) DETECTION METHOD AND DEVICE FOR DETECTING QUALITY OF OPTICAL ELEMENT

(75) Inventors: Hou-Ching Chin, Taipei (TW); Hsaing-Nan Chen, Taipei (TW)

(73) Assignee: Primax Electronics Ltd., Taipei (TW)

( * ) Notice: Subject to any disclaimer, the term of this patent is extended or adjusted under 35 U.S.C. 154(b) by 202 days.

(21) Appl. No.: 11/156,329

(22) Filed: Jun. 17, 2005

(65) Prior Publication Data

US 2006/0262298 A1  Nov. 23, 2006

(30) Foreign Application Priority Data

May 20, 2005  (TW) ............................... 94116423 A

(51) Int. Cl.
*G01B 9/00* (2006.01)
*G01N 21/00* (2006.01)

(52) U.S. Cl. .................... 356/124; 356/239.2; 348/127
(58) Field of Classification Search ........ 356/124–127, 356/239.1–239.8, 240.1; 348/127
See application file for complete search history.

(56) References Cited

U.S. PATENT DOCUMENTS

| | | | | | |
|---|---|---|---|---|---|
| 4,376,951 | A | * | 3/1983 | Miyazawa | 348/127 |
| 4,776,466 | A | * | 10/1988 | Yoshida | 209/565 |
| 5,216,481 | A | * | 6/1993 | Minato | 356/239.1 |
| 5,257,092 | A | * | 10/1993 | Noguchi et al. | 356/367 |
| 5,351,119 | A | * | 9/1994 | Nakatsue | 356/124 |
| 5,835,207 | A | * | 11/1998 | Sugiura et al. | 356/124 |
| 6,049,379 | A | * | 4/2000 | Lucas | 356/240.1 |

* cited by examiner

*Primary Examiner*—Hoa Q. Pham

(57) ABSTRACT

A detection method for detecting quality of an optical element includes the following steps. Firstly, a point light source is provided. Then, the point light source is allowed to penetrate through the optical element, thereby forming a first optical image on an optical image processing device. Then, the position of the optical element is adjusted when there is a shade block included in the first optical image, and the point light source is allowed to penetrate through the optical element after the adjusting step, thereby forming a second optical image on the optical image processing device. Afterward, the first optical image is compared with the second optical image to discriminate whether the shade block is synchronously moved with position adjustment of the optical element so as to realize the quality of the optical element.

16 Claims, 4 Drawing Sheets

DETECTION METHOD AND DEVICE FOR DETECTING QUALITY OF OPTICAL ELEMENT

FIELD OF THE INVENTION

The present invention relates to a detection method and a detection device for detecting the quality of an optical element, and more particularly to a detection method and a detection device for detecting the quality of an optical element by discriminating whether the optical path is obstructed with an obstructer remained in the optical lens.

BACKGROUND OF THE INVENTION

Since digital consumable electronic products have experienced great growth and are now rapidly gaining in popularity, these electronic products have attached thereto a photographing function. With the increasing development toward minimization, the overall volume of such a digital consumable electronic product becomes smaller and smaller. Accordingly, the volume of the camera module contained in the electronic product and the optical lens used in the camera module should be reduced.

For example, the procedure for detecting quality of this small-size optical lens is restricted because the mirror surface of the optical lens may be readily defected or contaminated when the mirror surface of the optical lens is scraped, there is any dust thereon or the material thereof is inhomogeneous.

Traditionally, the method for discriminating whether the mirror surface of the optical lens is defected or contaminated is performed by utilizing a high power microscope and a intense light to visually detect the mirror surface of the optical lens with the naked eye. This detection method, however, still has some drawbacks. For example, the obstructers obstructing the optical path and remained in the optical lens or other defects not readily visible to the naked eye fail to be effectively detected according to this method. Once the defective optical lens is mounted onto the electronic product, the resulting image quality would be unsatisfactory and the costs involving in post-control and maintenance would be increased.

In views of the above-described disadvantages resulted from the prior art, the applicant keeps on carving unflaggingly to develop a detection method and a detection device for detecting the quality of an optical element according to the present invention through wholehearted experience and research.

SUMMARY OF THE INVENTION

It is an object of the present invention to provide a detection method for easily detecting the quality of an optical element by discriminating whether the optical path is obstructed with an obstructer remained in the optical lens.

Another object of the present invention is to provide a detection device for easily detecting the quality of an optical element by discriminating whether the optical path is obstructed with an obstructer remained in the optical lens.

In accordance with a first aspect of the present invention, there is provided a detection method for detecting quality of an optical element. Firstly, a point light source is provided. Then, the point light source is allowed to penetrate through the optical element, thereby forming a first optical image on an optical image processing device. Then, the position of the optical element is adjusted when there is a shade block included in the first optical image, and the point light source is allowed to penetrate through the optical element after the adjusting step, thereby forming a second optical image on the optical image processing device. Afterward, the first optical image is compared with the second optical image to discriminate whether the shade block is synchronously moved with position adjustment of the optical element so as to realize the quality of the optical element.

Preferably, the point light source is a laser light source.

In an embodiment, the optical element includes an optical lens for penetrating the light emitted from the point light source therethrough and a lens clamp for holding the optical lens, wherein the lens clamp includes a position adjustable member for adjusting positions of the optical lens in a rotating or tilting manner.

In an embodiment, the shade block is formed by obstructing the optical path of the light emitted from the point light source with an obstructer remained in the optical element.

In an embodiment, the optical image processing device is a screen having a two dimension coordinate mark such that the first optical image and the second optical image are projected thereon.

In an embodiment, the quality of the optical element is unsatisfactory if the two dimension coordinate values of the shade block are synchronously moved with position adjustment of the optical element.

In an embodiment, the optical image processing device is a computer processing device having an optical sensing element for inputting the first optical image and the second optical image therevia.

In an embodiment, the quality of the optical element is unsatisfactory if the coordinate values of the shade block discriminated by the computer processing device are synchronously moved with position adjustment of the optical element.

In accordance with a second aspect of the present invention, there is provided a detection method for detecting quality of an optical element. Firstly, a point light source is provided. Then, the point light source is allowed to penetrate through the optical element, thereby forming different optical images on an optical image processing device when the optical element is arranged in different positions. Afterward, it is discriminated whether the shade blocks included in the optical images are identical so as to realize the quality of the optical element.

In accordance with a third aspect of the present invention, there is provided a detection device for detecting quality of an optical element. The detection device comprises a light-emitting element, a holding element and an optical image processing device. The light-emitting element is used for generating a point light source. The holding element is disposed downstream of the light-emitting element for holding an optical lens such that the point light source is allowed to penetrate therethrough the optical element, wherein the position of the optical lens is adjustable. The optical image processing device is disposed downstream of the holding element for processing different optical images generated when the optical element is arranged in different positions, and discriminates whether shade blocks included in the different optical images are synchronously moved with position adjustment of the optical lens so as to realize the quality of the optical lens.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
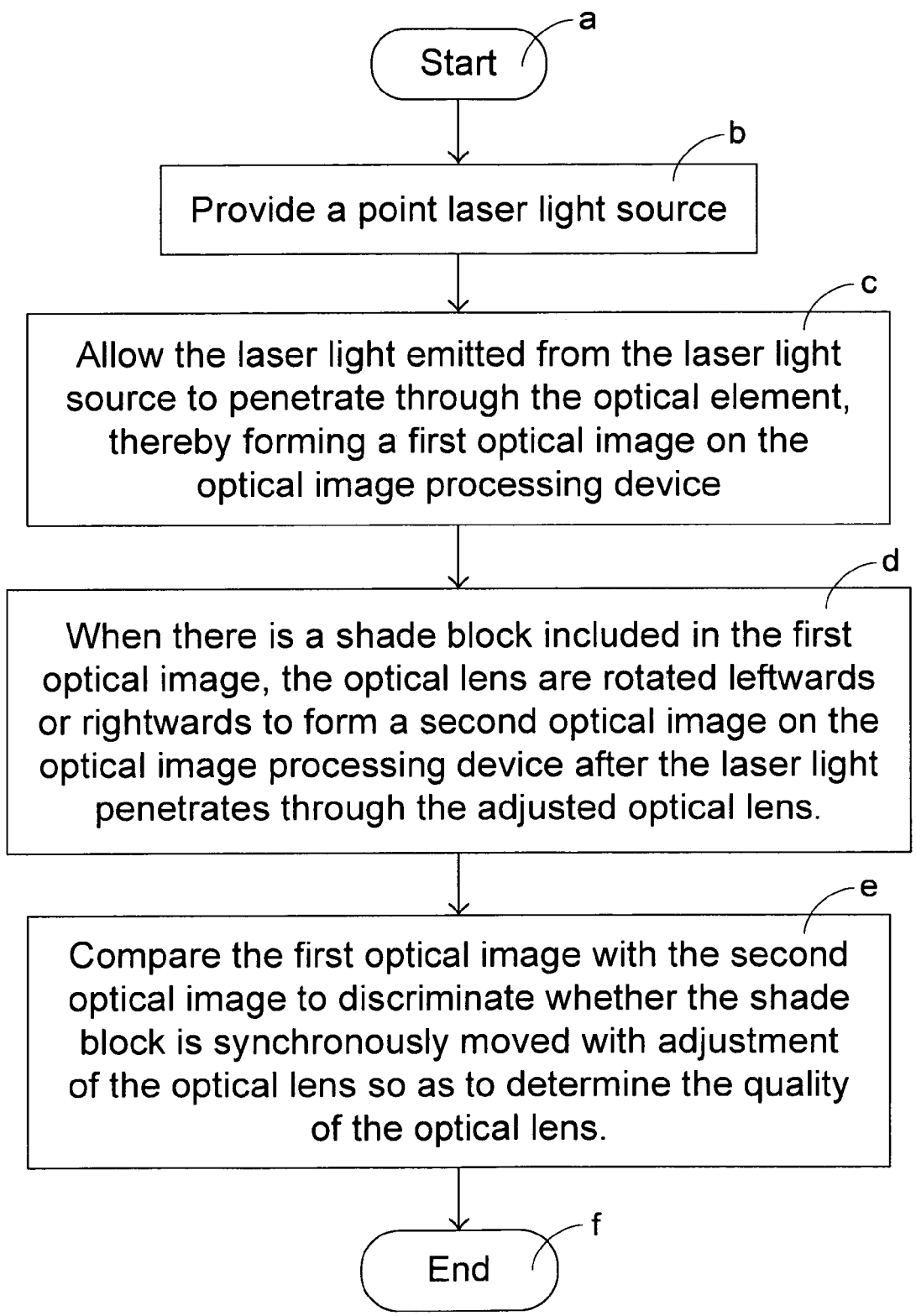
FIG. 1 is a flowchart illustrating a detection method for detecting the quality of an optical element according to an embodiment of the present invention.

Please refer to FIG. 1, which is a flowchart illustrating a detection method for detecting the quality of an optical element according to an embodiment of the present invention. The detection method comprises the following steps.

After the starting step (a), the step (b) of providing a point laser light source is performed.

Then, in the step (c), the laser light emitted from the laser light source is allowed to penetrate through the optical element, thereby forming a first optical image on the optical image processing device. An exemplary optical element described in the step (c) includes an optical lens for penetrating the laser light therethrough and a lens clamp for holding the optical lens. The lens clamp includes a position adjustable member for adjusting positions of the optical lens in a rotating or tilting manner.

In the step (d), when there is a shade block included in the first optical image, the optical lens are rotated leftwards or rightwards to form a second optical image on the optical image processing device after the laser light penetrates through the adjusted optical lens. The shade block is formed by obstructing the optical path of the laser light with an obstructer remained in the optical lens.

In the step (e), the first optical image is compared with the second optical image to discriminate whether the shade block is synchronously moved with position adjustment of the optical lens so as to realize the quality of the optical lens. An exemplary optical image processing device is a screen having a two dimension coordinate mark thereon. If the two dimension coordinate values of the shade block are synchronously moved with position adjustment of the optical lens, it is determined that the quality of the optical lens is unsatisfactory. Alternatively, the optical image processing device may be a computer processing device having an optical sensing element for inputting the first optical image and the second optical image therevia. Likewise, if the two dimension coordinate values of the shade block are synchronously moved with position adjustment of the optical lens, it is determined that the quality of the optical lens is unsatisfactory.

Afterward, the above procedures are terminated in the step (f).

Figure 2A:
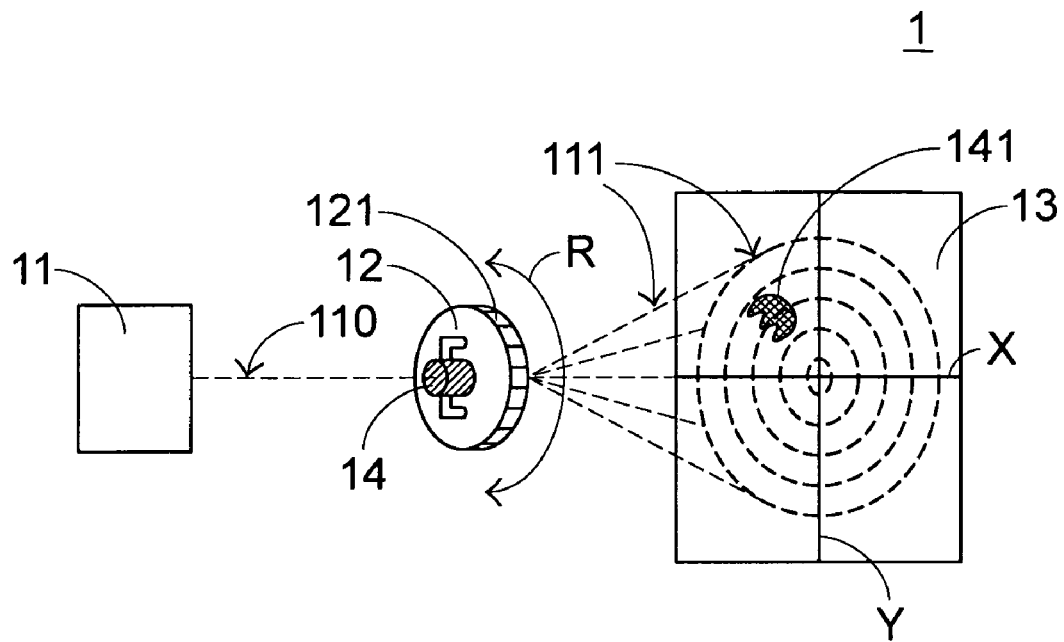
FIGS. 2(a) and 2(b) are schematic views illustrating a detection device for detecting quality of an optical element according to a first embodiment of the present invention.
Figure 2B:
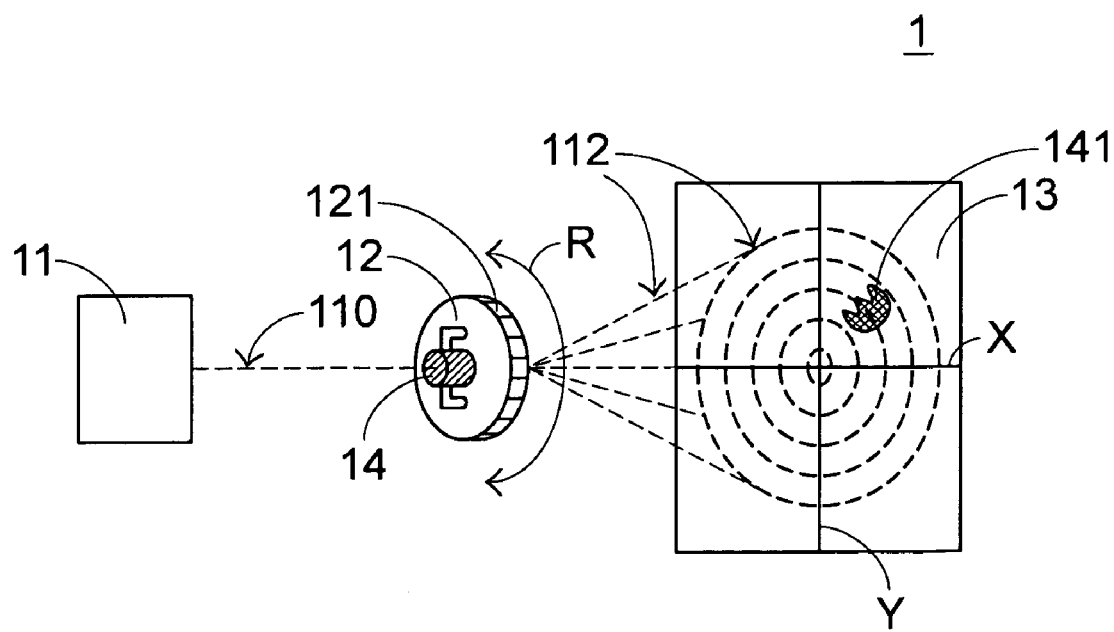

A schematic view of a detection device for detecting quality of an optical element according to a first embodiment of the present invention is illustrated with reference to FIGS. 2(a) and 2(b). The detection device 1 comprises a light-emitting element 11, a holding element 12 disposed downstream of the light-emitting element 11, and an optical image processing device 13 disposed downstream of the holding element 12. In an embodiment, the holding element 12 is a lens clamp having a position adjustable member 121, and the optical image processing device 13 is a screen having a two dimension coordinate mark thereon.

An optical lens 14 used to detect the optical quality thereof is clamped by the holding element 12. The point source light 110 (e.g. a laser light) generated from the light-emitting element 11 penetrates through the optical lens 14 and is then projected on the screen 13 having the two dimension coordinate mark thereon. When the optical lens 14 is located in a first position, the laser light 110 will penetrate through the optical lens 14 to project a first optical image 111 on the screen 13. The first optical image 111 includes a shade block 141 therein. By manually rotating the position adjustable member 121 such as a rotation element in a clockwise or anti-clockwise direction R, the optical lens 14 clamped by the holding element 12 is adjusted from the first position to a second position. When the optical lens 14 is located in the second position, the laser light 110 will penetrate through the optical lens 14 to project a second optical image 112 on the screen 13.

The two dimension coordinate values of the X-axis and the Y-axis are successively marked on the screen 13 with position adjustment of the position adjustable member 121. When the optical lens 14 is located in the first position and the first optical image is projected onto the screen in this circumstance, the shade block 141 may have a first coordinate value on the screen 13. On the other hand, when the optical lens 14 clamped by the holding element 12 is rotated to the second position, the shade block 141 of the second optical image 112 is also rotated to have a second coordinate value on the screen 13. Then, the appearance of the first optical image 111 is compared with that of the second optical image 112 to identify whether the shade blocks 141 are generated due to the obstructer in the optical lens 14. In other words, if the shade blocks 141 are generated due to the obstructer in the optical lens 14, the shade blocks 141 will be rotated to the prescribed coordinate values according to rotation of the optical lens 14. In this circumstance, the quality of the optical lens 14 will be realized according to the coordinate values.

Figure 3A:
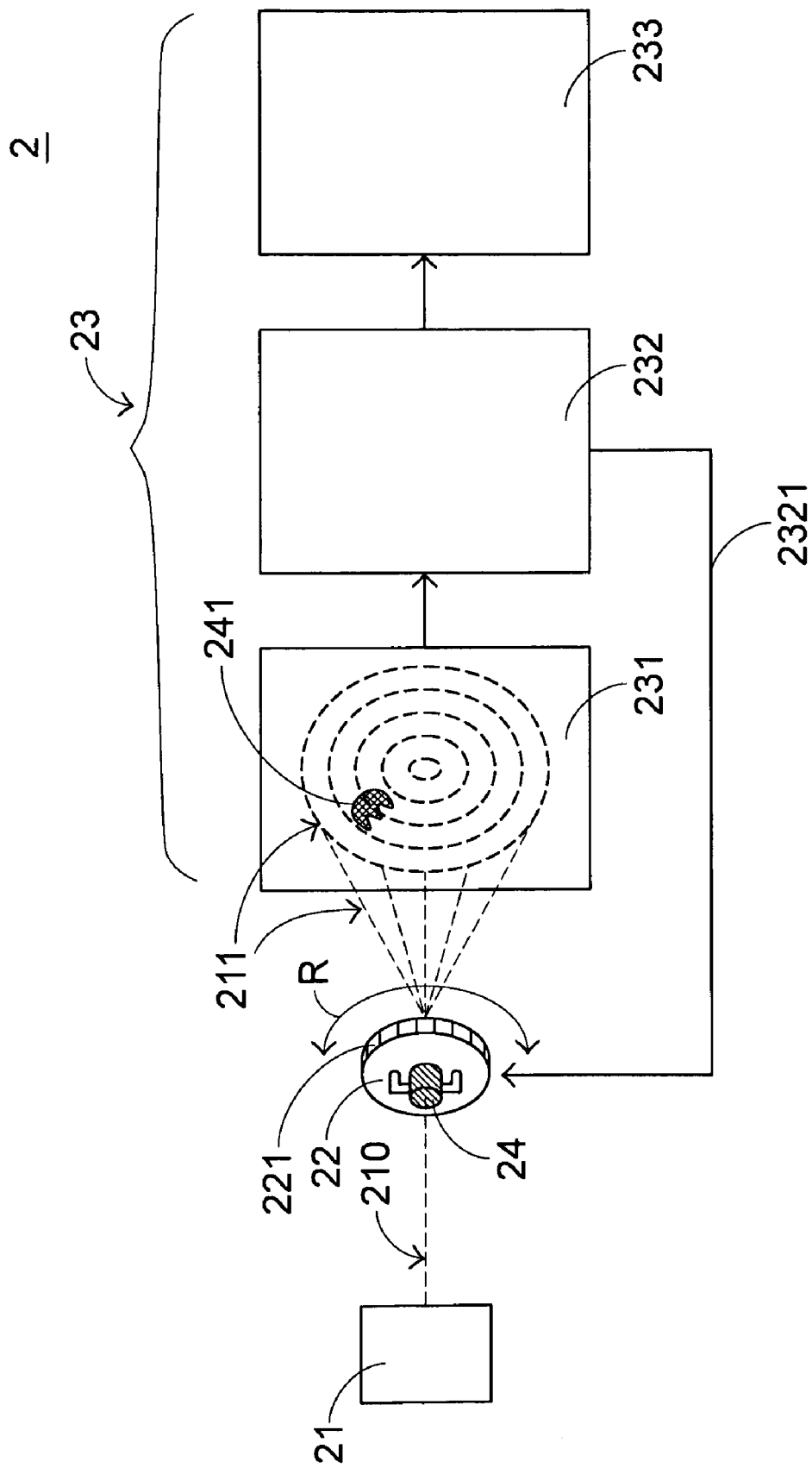
FIGS. 3(a) and 3(b) are schematic views illustrating a detection device for detecting quality of an optical element according to a second embodiment of the present invention.
Figure 3B:
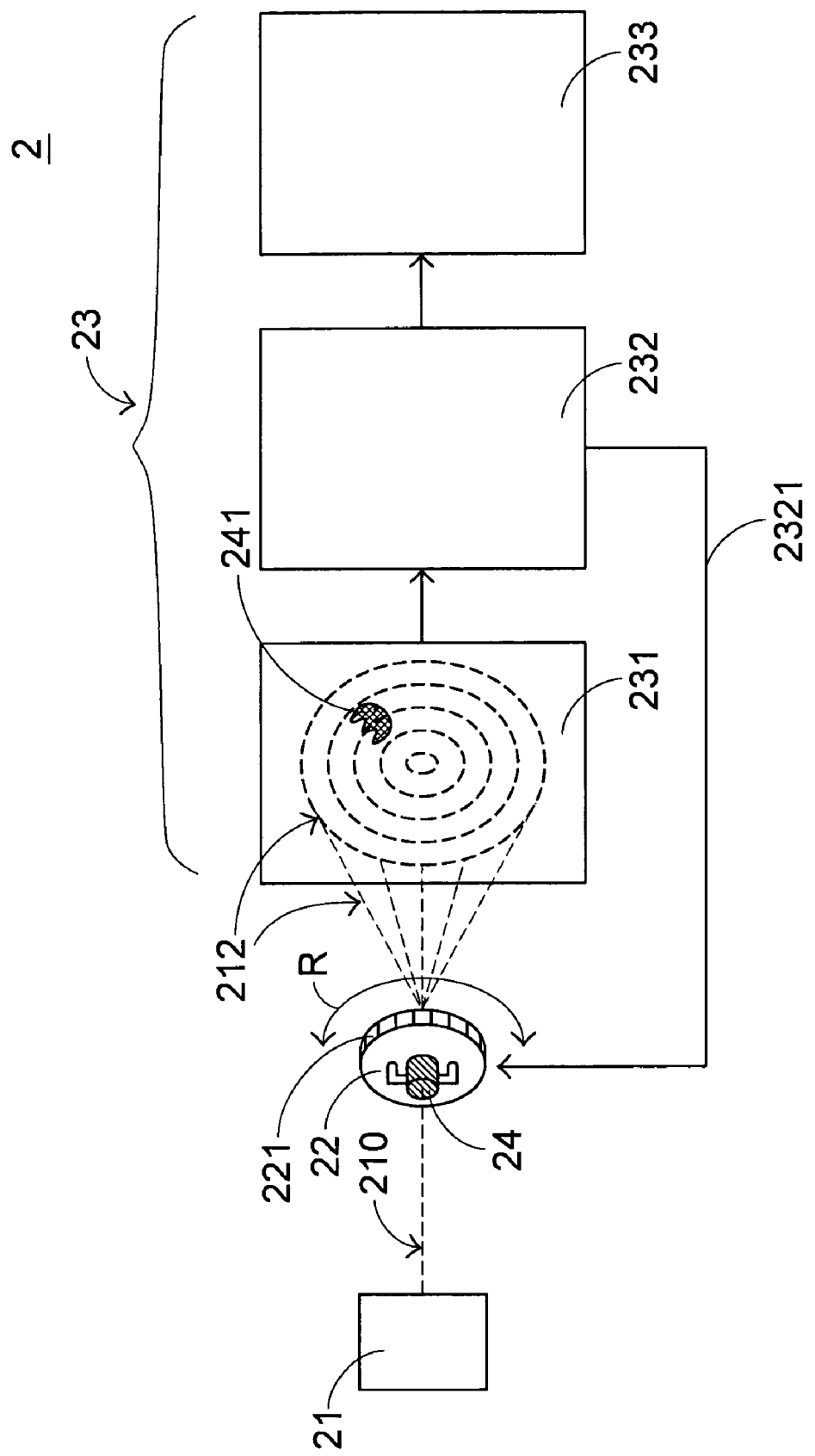

A schematic view of a detection device for detecting quality of an optical element according to a second embodiment of the present invention is illustrated with reference to FIGS. 3(a) and 3(b). The detection device 2 comprises a light-emitting element 21, a holding element 22 disposed downstream of the light-emitting element 21, and an optical image processing device 23 disposed downstream of the holding element 22. In an embodiment, the holding element 22 is a lens clamp having a position adjustable member 221, and the optical image processing device 23 is a computer processing device having an optical sensing element 231. An exemplary optical sensing element 231 is a charge coupled device (CCD). In addition to the optical sensing element 231, the optical image processing device 23 further comprises a microprocessor 232 and an output device 233. The microprocessor 232 is electrically connected to the optical sensing element 231 and the holding element 22. The output device 233 is electrically connected to the microprocessor 232. The operation principle of the optical sensing element 231 is known in the art, and is not to be redundantly described herein.

An optical lens 24 used to detect optical quality thereof is clamped by the holding element 22. The point source light 210 (e.g. a laser light) generated from the light-emitting element 21 penetrates through the optical lens 24 and is then projected on the optical sensing element 231. When the optical lens 24 is located in a first position, the laser light 210 will penetrate through the optical lens 24 to project a first optical image 211 on the optical sensing element 231. The first optical image 211 includes a shade block 241 therein. By rotating the position adjustable member 221 such as a rotation element in a clockwise or anti-clockwise direction R in response to a position adjusting signal generated from the microprocessor 232, the optical lens 24 clamped by the holding element 22 will be automatically adjusted from the first position to a second position. When the optical lens 24 is located in the second position, the laser light 210 will penetrate through the optical lens 24 to project a second optical image 212 on the optical sensing element 231.

The image signals sensed by the optical sensing element 231, i.e. the first optical image 211 and the second optical image 212, are inputted and processed by the microprocessor 232 and have two dimension coordinate values. When the optical lens 24 is located in the first position and the first optical image 211 is projected onto the optical sensing element 231 in this circumstance, the shade block 241 may have a first coordinate value on the optical sensing element 231.

On the other hand, when the optical lens 24 clamped by the holding element 22 is rotated to the second position, the shade block 241 of the second optical image 212 is also rotated to have a second coordinate value optical sensing element 231. Then, by means of the microprocessor 232, the appearance of the first optical image 211 will be compared with that of the second optical image 212 to identify whether the shade blocks 241 are generated due to the obstructer in the optical lens 24. In other words, if the shade blocks 241 are generated due to the obstructer in the optical lens 24, the shade blocks 241 projected onto the optical sensing element 231 will be rotated to the prescribed coordinate values according to rotation of the optical lens 24. In this circumstance, the quality of the optical lens 24 will be realized according to the coordinate values.

From the above description, the detection method and the detection device of the present invention are capable of easily detecting the quality of an optical element by discriminating whether the optical path is obstructed with an obstructer remained in the optical lens.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A detection method for detecting quality of an optical element, comprising steps of:
   providing a point light source;
   allowing said point light source to penetrate through said optical element, thereby forming a first optical image on an optical image processing device;
   adjusting the position of said optical element when there is a shade block included in said first optical image, and allowing said point light source to penetrate through said optical element after said adjusting step, thereby forming a second optical image on said optical image processing device; and
   comparing said first optical image with said second optical image to discriminate whether said shade block is synchronously moved with position adjustment of said optical element so as to realize the quality of said optical element.

2. The detection method for detecting quality of an optical element according to claim 1 wherein said point light source is a laser light source.

3. The detection method for detecting quality of an optical element according to claim 1 wherein said optical element includes an optical lens for penetrating the light emitted from said point light source therethrough and a lens clamp for holding said optical lens, wherein said lens clamp includes a position adjustable member for adjusting positions of said optical lens in a rotating or tilting manner.

4. The detection method for detecting quality of an optical element according to claim 1 wherein said shade block is formed by obstructing the optical path of the light emitted from said point light source with an obstructer remained in said optical element.

5. The detection method for detecting quality of an optical element according to claim 1 wherein said optical image processing device is a screen having a two dimension coordinate mark such that said first optical image and said second optical image are projected thereon.

6. The detection method for detecting quality of an optical element according to claim 5 wherein the quality of said optical element is unsatisfactory if the two dimension coordinate values of said shade block are synchronously moved with position adjustment of said optical element.

7. The detection method for detecting quality of an optical element according to claim 1 wherein said optical image processing device is a computer processing device having an optical sensing element for inputting said first optical image and said second optical image therevia.

8. The detection method for detecting quality of an optical element according to claim 7 wherein the quality of said optical element is unsatisfactory if the coordinate values of said shade block discriminated by said computer processing device are synchronously moved with position adjustment of said optical element.

9. A detection device for detecting quality of an optical element, comprising:
   a light-emitting element for generating a point light source;
   a holding element disposed downstream of said light-emitting element for holding an optical lens such that said point light source is allowed to penetrate therethrough said optical element, wherein the position of said optical lens is adjustable; and
   an optical image processing device disposed downstream of said holding element for processing different optical images generated when said optical element is arranged in different positions, and discriminating whether shade blocks included in said different optical images are synchronously moved with position adjustment of said optical lens so as to realize the quality of said optical lens.

10. The detection device for detecting quality of an optical element according to claim 9 wherein said point light source is a laser light source.

11. The detection device for detecting quality of an optical element according to claim 9 wherein said holding element is a lens clamp for holding said optical lens, and said lens clamp includes a position adjustable member for adjusting said different positions of said optical lens in a rotating or tilting manner.

12. The detection device for detecting quality of an optical element according to claim 9 wherein said shade blocks are formed by obstructing the optical path of the light emitted from said point light source with an obstructer remained in said optical lens.

13. The detection device for detecting quality of an optical element according to claim 9 wherein said optical image processing device is a screen having a two dimension coordinate mark such that said different optical images are projected thereon.

14. The detection device for detecting quality of an optical element according to claim 13 wherein the quality of said optical element is unsatisfactory if the two dimension coordinate values of said shade blocks are synchronously moved with position adjustment of said optical element.

15. The detection device for detecting quality of an optical element according to claim 9 wherein said optical image processing device is a computer processing device having an optical sensing element for inputting said different optical images therevia.

16. The detection device for detecting quality of an optical element according to claim 15 wherein the quality of said optical element is unsatisfactory if the coordinate values of said shade blocks discriminated by said computer processing device are synchronously moved with position adjustment of said optical element.

\* \* \* \* \*